United States Patent
Johnson et al.

(10) Patent No.: US 7,119,239 B2
(45) Date of Patent: *Oct. 10, 2006

(54) MANUFACTURE OF XYLENES USING REFORMATE

(75) Inventors: David L. Johnson, Clifton, VA (US); Robert G. Tinger, Friendswood, TX (US); Robert A. Ware, Wyndmoor, PA (US); John S. Buchanan, Lambertville, NJ (US); Xiaobing Feng, Houston, TX (US); Shifang Luo, Pittsford, NY (US); Gary D. Mohr, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 24 days.

This patent is subject to a terminal disclaimer.

(21) Appl. No.: 10/746,074

(22) Filed: Dec. 24, 2003

(65) Prior Publication Data

US 2004/0158111 A1 Aug. 12, 2004

Related U.S. Application Data

(63) Continuation-in-part of application No. 10/465,058, filed on Jun. 18, 2003.

(60) Provisional application No. 60/389,977, filed on Jun. 19, 2002.

(51) Int. Cl.
*C07C 2/66* (2006.01)

(52) U.S. Cl. ...................... 585/467; 585/469; 585/323; 585/322

(58) Field of Classification Search ................ 585/467, 585/469, 323, 322
See application file for complete search history.

(56) References Cited

U.S. PATENT DOCUMENTS

| | | |
|---|---|---|
| 3,354,078 A | 11/1967 | Miale et al. |
| 3,965,207 A | 6/1976 | Weinstein |
| 3,965,209 A | 6/1976 | Butter et al. |

(Continued)

FOREIGN PATENT DOCUMENTS

EP 0 174 121 3/1986

(Continued)

OTHER PUBLICATIONS

Poole, Charles P. Jr., "An Eletron Spin Resonance Study of Coke Deposits on a Silica-Alumina Catalyst," Journal of Catalysis, vol. 4, pp. 518-529, 1965.

(Continued)

*Primary Examiner*—Thuan Dinh Dang
(74) *Attorney, Agent, or Firm*—Xiaobing Feng

(57) ABSTRACT

A process is provided for the production of xylenes from reformate. The process is carried out by methylating under conditions effective for the methylation, the benzene/toluene present in the reformate outside the reforming loop, to produce a resulting product having a higher xylenes content than the reformate. Greater than equilibrium amounts of para-xylene can be produced by the process.

34 Claims, 2 Drawing Sheets

U.S. PATENT DOCUMENTS

| | | | |
|---|---|---|---|
| 3,965,210 A | | 6/1976 | Chu |
| 4,002,697 A | | 1/1977 | Chen |
| 4,076,842 A | | 2/1978 | Plank et al. |
| 4,100,215 A | | 7/1978 | Chen |
| 4,240,898 A | * | 12/1980 | Gomi ..................... 208/40 |
| 4,283,306 A | | 8/1981 | Herkes |
| 4,289,607 A | | 9/1981 | Kokotailo |
| 4,358,362 A | | 11/1982 | Smith et al. |
| 4,358,363 A | | 11/1982 | Smith |
| 4,377,718 A | * | 3/1983 | Sato et al. ................. 585/467 |
| 4,380,685 A | | 4/1983 | Chu |
| 4,670,616 A | | 6/1987 | De Simone et al. |
| 4,849,515 A | | 7/1989 | Matier et al. |
| 4,849,575 A | | 7/1989 | Lewis |
| 4,975,178 A | * | 12/1990 | Clem et al. ................. 208/65 |
| 5,043,502 A | | 8/1991 | Martindale et al. |
| 5,118,896 A | | 6/1992 | Steigelmann et al. ....... 585/467 |
| 5,349,113 A | | 9/1994 | Chang et al. |
| 5,816,322 A | | 10/1998 | Albano et al. |
| 5,865,986 A | | 2/1999 | Buchanan et al. ........... 208/65 |
| 5,993,642 A | | 11/1999 | Mohr et al. |
| 5,994,603 A | | 11/1999 | Mohr et al. |
| 5,998,686 A | * | 12/1999 | Clem et al. ................. 585/415 |
| 6,153,089 A | * | 11/2000 | Das et al. ................... 208/134 |
| 6,294,493 B1 | | 9/2001 | Strohmaier et al. |
| 6,388,156 B1 | | 5/2002 | Ou et al. |
| 6,423,879 B1 | * | 7/2002 | Brown et al. ............... 585/467 |

FOREIGN PATENT DOCUMENTS

| | | |
|---|---|---|
| JP | 09 208502 | 8/1997 |
| WO | WO 96/16004 | 5/1996 |
| WO | WO 98/09928 | 3/1998 |
| WO | WO 98/14415 | 4/1998 |
| WO | WO 99/38823 | 8/1999 |
| WO | WO 01/32591 | 5/2001 |
| WO | WO01/32591 | 5/2001 |
| WO | WO 2004/000974 | 12/2003 |

OTHER PUBLICATIONS

Miale, J.N.., "*Catalysis by Crystalline Aluminosilicates*," *Journal of Catalysis*, vol. 6, p. 278, 1996.

Olson, D.H., "*Chemical and Physical Properties of the ZSM-5 Substitutional Series*," *Journal of Catalysis*, vol. 61, pp. 390-396, 1980.

* cited by examiner

MANUFACTURE OF XYLENES USING REFORMATE

REFERENCE TO RELATED APPLICATIONS

This application is a continuation-in-part of application Ser. No. 10/465,058, filed Jun. 18, 2003, which claims priority to provisional application Ser. No. 60/389,977, filed Jun. 19, 2002.

BACKGROUND OF THE INVENTION

1. Field of the Invention

This invention relates to a process for producing xylenes using reformate by methylating the benzene and/or toluene contained in the reformate to produce xylenes.

2. Description of the Prior Art

Most aromatics production is based on the recovery of aromatics derived from catalytic reforming of naphtha. That process, using a feed containing a $C_{6+}$ hydrocarbons, typically produces a reformate comprised of $C_6$–$C_8$ aromatics along with paraffins and heavier aromatics.

Aromatics can also be produced by the dehydrocyclo-oligomerization of $C_2$–$C_5$ aliphatic hydrocarbons. That process typically produces a product comprised of benzene, toluene, xylenes, $C_{5+}$ paraffins, $C_{4-}$ light paraffins, olefins, and unreacted $C_2$–$C_5$ aliphatic hydrocarbons.

Another technique for producing aromatics involves the cracking of hydrocarbons such as by steam cracking or catalytic cracking. That process typically produces a product comprised of benzene, toluene, xylenes, $C_{6+}$ paraffins, and other hydrocarbons. Normally, the aromatics present in the reformate stream from a reformer or cracker will depend on the composition of the feedstock to the reformer or cracker, the type of reformer or cracker, and the operating conditions of the reformer or cracker. Normally, the aromatics present in the reformate stream will comprise benzene, toluene, a near equilibrium mixture of xylenes, ethylbenzene, and a mixture of nominally of $C_9$–$C_{10}$. Products of the reformate having the most value are benzene and xylenes. Of the xylene isomers, i.e., ortho-, meta- and para-xylene, the para-xylene is of particular value as a large volume chemical intermediate in a number of applications, such as the manufacture of terephthalic acid, which is an intermediate in the manufacturer of polyester.

The reformate is usually sent to an aromatics recovery complex where it undergoes several processing steps in order to recover high value products, e.g., xylenes and benzene, and to convert lower value products, e.g., toluene, into higher value products. For example, the aromatics present in the reformate are usually separated into different fractions by carbon number; e.g. benzene, toluene, xylenes, and ethylbenzene, etc. The $C_8$ fraction is then subjected to a processing scheme to make more high value para-xylene. Para-xylene is usually recovered in high purity from the $C_8$ fraction by separating the para-xylene from the ortho-xylene, meta-xylene, and ethylbenzene using selective adsorption or crystallization. The ortho-xylene and meta-xylene remaining from the para-xylene separation are isomerized to produce an equilibrium mixture of xylenes. The ethylbenzene is isomerized into xylenes or is dealkylated to benzene and ethane. The para-xylene is then separated from the ortho-xylene and the meta-xylene using adsorption or crystallization and the para-xylene-deleted-stream is recycled to extinction to the isomerization unit and then to the para-xylene recovery unit until all of the ortho-xylene and meta-xylene are converted to para-xylene and recovered.

Toluene is typically recovered as a separate fraction and then may be converted into higher value products, e.g., benzene and/or xylenes. One toluene conversion process involves the disproportionation of toluene to make benzene and xylenes. Another process involves the hydrodealkylation of toluene to make benzene.

Both toluene disproportionation and toluene hydrodealkylation result in the formation of benzene. With the current and future anticipated environmental regulations involving benzene, it is desirable that the toluene conversion not result in the formation of significant quantities of benzene.

Xylenes can be produced by the methylation of toluene. Such a process is disclosed in U.S. Pat. No. 3,965,207. One advantage of producing xylenes by this process is that the xylenes production does not result in the formation of benzene by-product.

The recovery of toluene from reformate as a separate fraction requires several processing steps. Typically, after removal of hydrogen and the $C_1$–$C_5$ and $C_{8+}$ fractions, the $C_6$–$C_7$ aromatics (benzene and toluene) are separated from the $C_6$–$C_8$ non-aromatics such as $C_6$–$C_8$ paraffins, $C_6$–$C_8$ olefins, and $C_6$–$C_8$ naphthenes by aromatics extraction. The toluene is then separated by distillation from the benzene and then sent to a toluene methylation unit to undergo toluene methylation to produce xylenes. A problem associated with this technique is that the aromatics extraction step can add significantly to the cost of producing of xylenes via toluene methylation. Also, a bottleneck condition can occur if the extraction capacity of the aromatics extraction unit does not accommodate the reaction capacity of the toluene methylation unit. Further, separation of toluene from reformate as a separate fraction may require substantial capital investment in additional equipment, e.g., benzene/toluene recovery unit and xylenes recovery unit etc.

The present invention is directed to a process for producing xylenes using reformate by toluene methylation which overcomes or at least mitigates one or more of the above-described problems.

SUMMARY OF THE INVENTION

In accordance with the present invention, there is provided a process for producing xylenes using reformate, which process comprises:

(a) providing a reformate containing hydrogen, $C_1$–$C_5$ hydrocarbons, $C_6$–$C_7$ hydrocarbons comprising benzene, toluene or mixtures thereof, and $C_{8+}$ hydrocarbons;

(b) removing at least a portion of said hydrogen from said reformate to produce a product having less hydrogen content than said reformate; and (c) methylating at least a portion of the benzene, toluene, or mixtures thereof present in said product in a methylation reaction zone with a methylating agent under conditions effective for the methylation and in the presence of a catalyst effective for the methylation to produce a resulting product having a higher xylenes content than said reformate.

In the practice of the present invention according to the above-described embodiment, usually at least a portion of the $C_1$–$C_5$ hydrocarbons present in the reformate is removed before methylation takes place.

In another embodiment, the present invention provides a process for producing xylenes using reformate formed in an aromatization zone, which process comprises the step of:

(a) providing a reformate containing hydrogen, $C_1$–$C_5$ hydrocarbons, $C_6$–$C_7$ hydrocarbons comprising benzene, toluene or mixtures thereof, and $C_{8+}$ hydrocarbons;

(b) removing at least a portion of said hydrogen from said reformate to produce a first product having less hydrogen content than said reformate;

(c) removing at least a portion of said $C_1$–$C_5$ hydrocarbons from said first product in a $C_1$–$C_5$ hydrocarbon separation zone to produce a second product having less $C_1$–$C_5$ hydrocarbon content than said first product;

(d) removing at least a portion of said $C_{8+}$ hydrocarbons from said second product in a $C_{8+}$ hydrocarbon separation zone to produce a third product having less $C_{8+}$ hydrocarbons content than said second product;

(e) transferring at least a portion of said third product to a methylation reaction zone; and, (f) methylating in said methylation reaction zone at least a portion of the benzene, toluene, or mixtures thereof present in said third product with a methylating agent under conditions effective for the methylation and in the presence of a catalyst effective for the methylation to produce a fourth product having a higher xylenes content than said reformate.

In a further embodiment, the present invention provides a process for producing xylenes using reformate formed in an aromatization zone, which process comprises the step of:

(a) providing a reformate containing hydrogen, $C_1$–$C_5$ hydrocarbons, $C_6$–$C_7$ hydrocarbons comprising benzene, toluene or mixtures thereof, and $C_{8+}$ hydrocarbons;

(b) removing at least a portion of said hydrogen from said reformate to produce a first product having less hydrogen content than said reformate;

(c) removing at least a portion of said $C_{8+}$ hydrocarbons from said first product in a $C_8$+hydrocarbon separation zone to produce a second product having less $C_{8+}$ hydrocarbon content than said first product;

(d) transferring at least a portion of said second product to a methylation reaction zone; and, (e) methylating in said methylation reaction zone at least a portion of the benzene, toluene, or mixtures thereof present in said second product with a methylating agent under conditions effective for the methylation and in the presence of a catalyst effective for the methylation to produce a third product having a higher xylenes content than said reformate.

In still another embodiment, the present invention provides a process for producing xylenes using reformate formed in an aromatization zone, which process comprises the step of:

(a) providing a reformate comprising: (i) hydrogen; (ii) $C_1$–$C_5$ hydrocarbons, (iii) $C_6$–$C_7$ aromatic hydrocarbons comprising benzene, toluene or mixtures thereof, (iv) $C_{8+}$ aromatic hydrocarbons; and, (v) up to 70 weight percent of non-aromatic $C_6$–$C_8$ hydrocarbons based on the weight of the $C_6$–$C_7$ hydrocarbons present in the feed stream;

(b) methylating at least a portion of said benzene, toluene, or mixtures thereof present in said reformate in a methylation reaction zone with a methylating agent under conditions effective for the methylation and in the presence of an acidic molecular sieve catalyst to produce a product containing a reduced amount of $C_6$–$C_8$ non-aromatic hydrocarbons compared to the reformate and xylenes.

In this embodiment, preferably the acidic molecular sieve catalyst is para-selective and at least 60 percent of the xylenes produced in the methylation are para-xylene. Further, preferably at least a portion of the hydrogen, the $C_1$–$C_5$ hydrocarbons, and the $C_{8+}$ aromatic hydrocarbons are removed from said reformate before methylation. Most preferably, substantially all of the $C_1$–$C_5$ hydrocarbons and the $C_{8+}$ aromatic hydrocarbons are removed from said reformate before methylation.

The methylation reaction can occur in the liquid phase or the vapor phase. Usually the reaction will occur in the vapor phase. The presence of the vapor phase in the reactor zone results in increased catalytic activity in the reactor zone and increased diffusion of molecules to the catalytic sites of the catalyst, e.g., pores of the molecular sieve. The expression "vapor phase", as used herein, includes the presence of minor amounts of some liquid phase, e.g., less than 10 percent by volume of liquid, as well as the substantial absence of liquid phase.

DETAILED DESCRIPTION OF THE INVENTION

The term "aromatization", as used herein, shall mean the production of aromatics comprising benzene, toluene, or mixtures thereof by the conversion of non-aromatic hydrocarbons to aromatic hydrocarbons comprising benzene, toluene, or mixtures thereof. The term "aromatization", as used herein, shall also include the production of aromatics comprising benzene, toluene, or mixtures thereof by the cracking of heavy aromatic hydrocarbons to produce the aromatic hydrocarbons comprising benzene, toluene, or mixtures. Examples of aromatization processes include catalytic reforming of naphtha, dehydrocyclo-oligomerization of $C_2$–$C_5$ aliphatic hydrocarbons, steam cracking of hydrocarbons to produce aromatic hydrocarbons comprising benzene, toluene, or mixtures thereof, and the catalytic cracking of hydrocarbons to produce aromatic hydrocarbons comprising benzene, toluene, or mixtures thereof.

The term "reformate", as used herein, shall mean the product produced by "aromatization".

Figure 1:
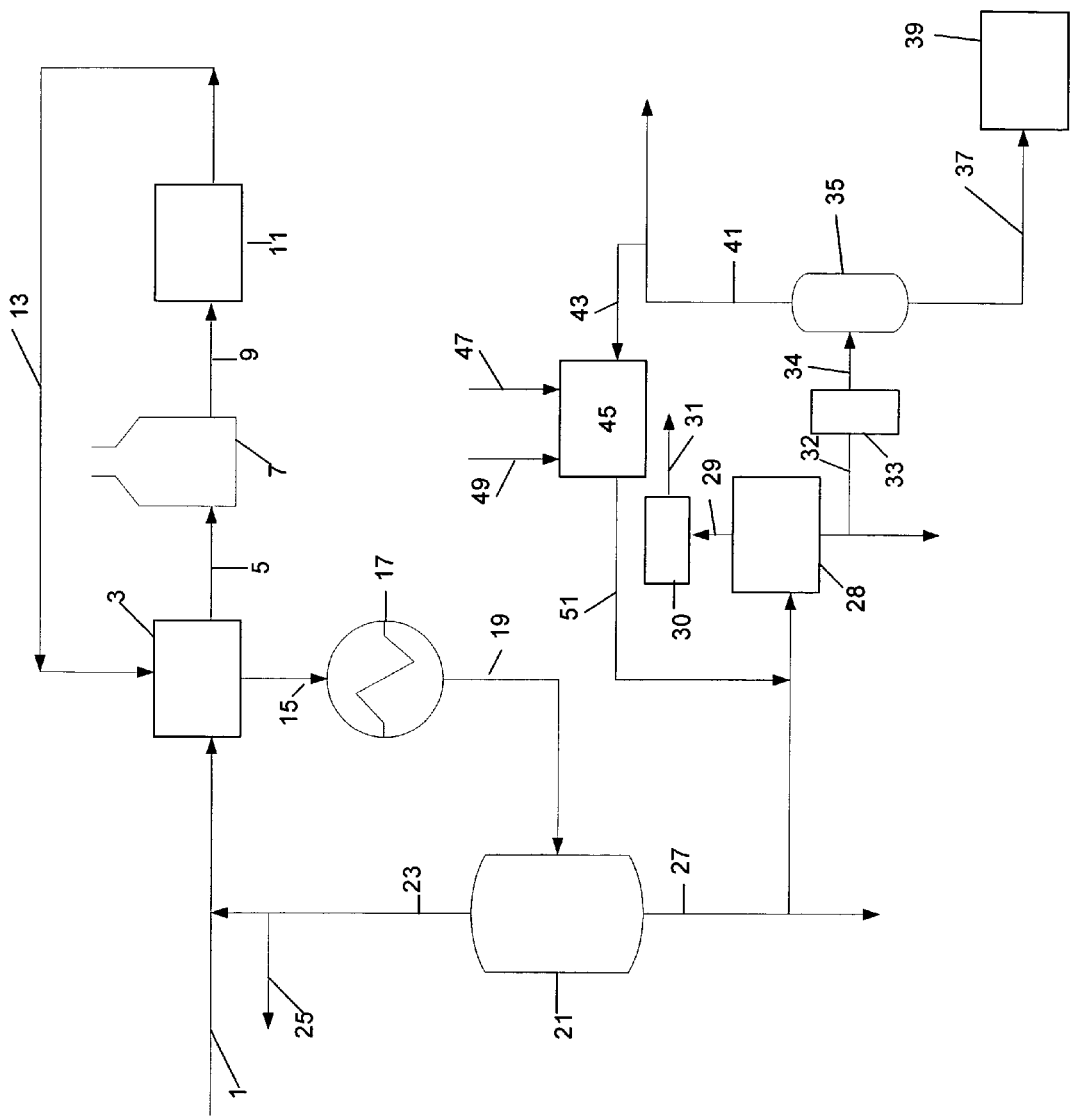
FIG. 1 is a simplified process flow diagram, illustrating an embodiment of the invention.

FIG. 1 illustrates an embodiment of the invention, in simplified form, where the $C_6$/$C_7$ fraction from the reformate is methylated in a reaction zone located outside the reforming loop. Referring to FIG. 1, naphtha is directed via line 1 to heat exchanger 3 where the temperature of the naphtha is elevated. The naphtha feed can be either naphtha alone or the naphtha can be combined with toluene. Next, the heated naphtha is sent via line 5 to reformer heater 7 which elevates the temperature of the feed to a temperature suitable for reforming. After heating, the naphtha is withdrawn via line 9 to aromatization reactor zone 11 where the naphtha is reformed into aromatic products. Although only one reactor zone is shown, there can be more than one reactor zone. The reformate is then withdrawn and sent via line 13 to heat exchanger 3. Heat exchanger 3 cools the reformate and uses the heat recovered from the reformate to elevate the temperature of the naphtha supplied via line 1. Next, the reformate is withdrawn through line 15 to heat exchanger 17 to further cool the reformate for separation of hydrogen from the product. Next, the cooled reformate is sent via line 19 to high pressure separator 21 where hydrogen is recovered. Hydrogen is removed via line 23 and either recycled back to the reforming unit or removed from the system via line 25. Next, the product is sent via line 27 to separation block 28 where low pressure hydrogen, $C_4-$ and $C_5$ are separated and removed from the product. The hydrogen and $C_4-$ and $C_5$ hydrocarbons are then sent via line 29 to oxygenate/water removal unit 30. After separation of oxygenates and water, the hydrogen and $C_4-$ and $C_5$ hydrocarbons are removed from oxygenate/water removal unit 30 via line 31. The $C_{6+}$ product, including benzene and toluene, is sent via line 32 to oxygenate/water removal unit 33. After removal of the oxygenates and water, the $C_{6+}$ product is supplied via line 34 to distillation column 35. The $C_{8+}$ fraction is removed from the bottom of distillation column 35 via line 37 and further separated and converted in xylene loop 39 to the desired molecules, e.g., para-xylene and other by-products. The $C_6/C_7$ fraction, including benzene and toluene, is removed from distillation column 35 overhead via line 41. Next, either part or all of the $C_6/C_7$ fraction is supplied via line 43 to methylation reaction zone 45. If desired, a stream of hydrocarbons comprised of benzene and/or toluene can be added to the $C_6/C_7$ fraction. The methylation reaction can be carried out in the vapor phase. When carried out in the vapor phase, the $C_6/C_7$ fraction can be heated either before it enters the methylation reaction zone or after it has entered the methylation reaction zone. The methylating agent can be supplied to methylation reaction zone 45 via line 47. Also, hydrogen-containing gas can be supplied to methylation reaction zone 45 via line 49. The methylating agent is preferably supplied to methylation reaction zone 45 through a plurality of feed points, e.g., 3–6 feed points. In methylation reaction zone 45, the toluene present in the $C_6/C_7$ fraction is methylated to form xylenes. Also, benzene present in the $C_6/C_7$ fraction can be methylated to form toluene which, in turn, can be methylated to form xylenes. The catalyst used in the methylation reaction zone 45 for the methylation can be any catalyst effective for toluene or benzene methylation, e.g., catalyst that produces equilibrium amounts of para-xylene, or one that is selective to produce greater than equilibrium amounts of a desired xylene isomer, e.g., para-xylene. The methylated product is then sent via line 51 and mixed with the product in line 27 to separation block 29. After leaving separation block 29 via line 33, the methylated product is processed in distillation column 35 and then sent to xylene loop 39. Practicing the invention according to this embodiment allows sharing of the low pressure separator, the benzene/toluene recovery unit and xylenes recovery unit.

As shown in FIG. 1, the methylation reaction zone is located to receive the $C_6/C_7$ fraction from distillation column 35. For some operations, it may be particularly useful for the methylation reaction zone to be located between high pressure separator 21 and separation block 29. In this configuration, the methylation reaction zone will receive part or all of the reformate in which a portion of hydrogen has been removed. After leaving the methylation reaction zone, the methylated product will be sent to separation block 29 and further processed. Also, for some operations, it may particularly useful for the methylation reaction zone to be located between separation block 29 and distillation column 35. In this embodiment, the methylation reaction zone will receive at least a portion of the reformate in which at least a portion of the hydrogen, $C_6-$, and $C_5-$ have been removed. After leaving the methylation reaction zone, the methylated product is sent to separation block 29 and further processed.

Figure 2:
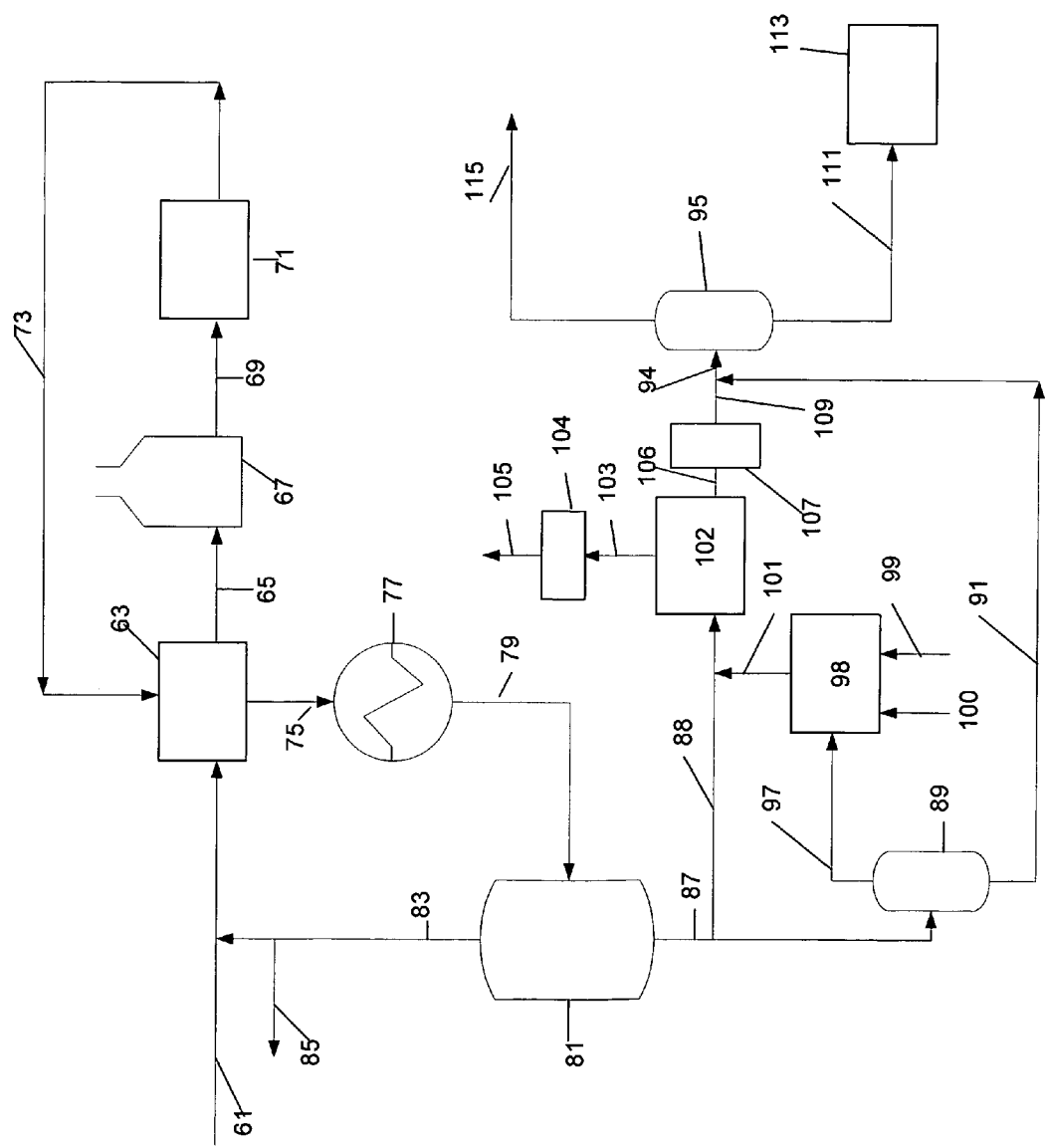
FIG. 2 is a simplified process flow diagram, illustrating another embodiment of the invention.

FIG. 2 illustrates another embodiment of the invention, in simplified form, where the methylation reaction takes place outside the reforming loop. In this embodiment, at least a portion of the hydrogen and $C_{8+}$ fraction is removed from the reformate and then the resulting product is sent to the toluene methylation unit. Referring to FIG. 2, naphtha is directed via line 61 to heat exchanger 63 where the temperature of the naphtha is elevated. The naphtha feed can be either naphtha alone or the naphtha can be combined with toluene. Next, the heated naphtha is sent via line 65 to reformer heater 67 which elevates the temperature of the feed to a temperature suitable for reforming. After heating, the naphtha is withdrawn via line 69 to aromatization reactor zone 71 where the naphtha is reformed into aromatic products. Although only one reactor zone is shown, there can be more than one reactor zone. The reformate is then withdrawn and sent via line 73 to heat exchanger 63. Heat exchanger 63 cools the reformate and uses heat recovered from the reformate to elevate the temperature of the naphtha supplied via line 61. Next, the reformate is withdrawn through line 75 to heat exchanger 77 to further cool the reformate for separation of hydrogen from the product. Next, the cooled reformate is sent via line 79 to high pressure separator 81 where hydrogen is recovered. Hydrogen is removed via line 83 and either recycled back to the reforming unit or removed from the system via line 85. Next, the product is sent via line 87 to $C_{8+}$ separator 89 where at least a portion of the $C_{8+}$ fraction is separated and removed from the bottom of separator 89 and sent to distillation column 95 via lines 91 and 94. Any product not sent to separator 89 can be sent via line 88 to separation block 102. The $C_7-$ fraction is removed overhead from separator 89 and supplied via line 97 to methylation reaction zone 98. If desired, a stream of hydrocarbons comprised of benzene and/or toluene can be added to the reformate. The methylation reaction can be carried out in the vapor phase. When carried out in the vapor phase, the $C_7-$ fraction can be heated either before it enters the methylation reaction zone or after it has entered the methylation reaction zone. The methylating agent can be supplied to methylation reaction zone 98 via line 99. Also, hydrogen-containing gas can be supplied to methylation reaction zone 98 via line 100. The methylating agent is preferably supplied to methylation reaction zone 98 through a plurality of feed points, e.g., 3–6 feed points. The methylated product is then sent via line 101 to separation block 102 where low pressure hydrogen, $C_4-$ and $C_5$ are separated and removed from the product. The hydrogen and $C_4-$ and $C_5$ hydrocarbons removed via line 103 to oxygenate/water removal unit 104. After separation of oxygenates and water, the hydrogen and $C_4-$ and $C_5$ hydrocarbons are removed from oxygenate/water removal unit 104 via line 105. The $C_{6+}$ product, including benzene and toluene, is sent via line 106 to oxygenate/water removal unit 107. The resulting product, $C_{6+}$, including benzene and toluene, is supplied via line 109 and line 94 to distillation column 95. The $C_{8+}$ fraction is removed from the bottom of distillation column 95 via line 111 and further separated and converted in xylene loop 113 to the desired molecules, e.g., para-xylene and other by-products. The $C_6/C_7$ fraction, including benzene and toluene, is removed from distillation column 95 overhead via line 115. Practicing the invention according to this embodiment allows sharing of the low pressure separator, the benzene/toluene recovery unit and xylenes recovery unit.

Aromatization

Aromatization will usually be carried out by catalytic reforming of naphtha or the dehydrocyclo-oligomerization of $C_2$–$C_5$ aliphatics.

Dehydrocyclo-oligomerization involves converting $C_2$–$C_5$ aliphatic hydrocarbons to aromatic hydrocarbons. The process is carried out by contacting $C_2$–$C_5$ aliphatic hydrocarbons in an aromatization zone and in the presence of a catalyst suitable for dehydrocyclodimerization and under conditions effective to produce a aromatics product comprising benzene and/or toluene. The dehydrocyclodimerization process increases carbon chain length by oligomerization, promotes cyclization, and dehydrogenates cyclics to their respective aromatics.

The feedstream used in the dehydrocyclo-oligomerization process will contain at least one aliphatic hydrocarbon containing 2 to about 5 carbon atoms. The aliphatic hydrocarbons may be open chain, straight chain, or cyclic. Examples such as hydrocarbons include ethane, ethylene, propane, propylene, n-butane, n-butenes, isobutane, isobutene, butadiene, straight and branch pentane, pentene, and pentyldiene. Dehydrocyclo-oligomerization conditions will vary depending on such factors as feedstock composition and desired conversion. A desired range of conditions for the dehydro-cyclodimerization of the aliphatic hydrocarbons to aromatics include a temperature from about 350° to about 650° C., a pressure from about 1 to about 100 atmospheres, and weight hour space velocity from about 0.2 to about 8. It is understood that, as the average carbon number of the feed increases, a temperature in the lower end of temperature range is required for optimum performance and conversely, as the average carbon number of the feed decreases, the higher the required reaction temperature.

The catalyst used in the dehydrocyclo-oligomerization reaction will preferably comprise an intermediate pore size molecular sieve. Intermediate pore size molecular sieves have a pore size from about 5 to about 7 Å and include, for example, AEL, AFI, MWW, MFI, MEL, MFS, MEI, MTW, EUO, MTT, HEU, FER, and TON structure type molecular sieves. These materials are described in "Atlas of Zeolite Structure Types", eds. W. H. Meier, D. H. Olson, and Ch. Baerlocher, Elsevier, Fourth Edition, 1996, which is hereby incorporated by reference. Examples of suitable intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-5. Preferred molecular sieves are SAPO-11, as well as titanosilicate, gallosilicate, aluminosilicate, and gallium-containing aluminosilicate molecular sieves having a MFI structure.

Usually the molecular sieve will be combined with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642, which is hereby incorporated by reference.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 20 to about 50 percent.

To make enhanced amounts (greater than equilibrium amounts) of para-xylene (versus the other xylene isomers produced by the dehydrocyclo-oligomerization reaction), a molecular sieve catalyst, e.g., ZSM-5 catalyst, can be selectivated by the use of a selectivating agent.

Examples of compounds for selectivating the catalysts include treating the surface of the catalyst with compounds of phosphorus and/or various metal oxides such as alkaline earth metal oxides, e.g., calcium oxide, magnesium oxide, etc. rare earth metal oxides, lanthanum oxide, and other metal oxides such as boron oxide, titania, antimony oxide, and manganese oxide.

Selectivation may also be accomplished by depositing coke on the catalyst. The coke selectivation can be carried out during the methylation reaction such as by running the methylation reaction at conditions which allow the deposition of coke on the catalyst. Also, the catalyst can be preselectivated with coke such as by exposing the catalyst in the reactor to a thermally decomposable organic compound, e.g., benzene, toluene, etc. at a temperature in excess of the decomposition temperature of said compound, e.g., from about 400° C. to about 650° C., more preferably 425° C. to about 550° C., at a WHSV in the range of from about 0.1 to about 20 lbs. of feed per pound of catalyst per hour, at a pressure in the range of from about 1 to about 100 atmospheres, and in the presence of 0 to about 2 moles of hydrogen, more preferably from about 0.1 to about 1 moles of hydrogen per mole of organic compound, and optionally in the presence of 0 to about 10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke.

Selectivation of the catalyst may also be accomplished using organosilicon compounds. The silicon compounds may comprise a polysiloxane include silicones, a siloxane, and a silane including disilanes and alkoxysilanes.

Silicone compounds that can be used in the present invention include the following:

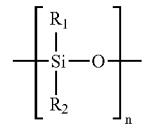

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclotetrasiloxane, hexaphenylcyclotrisiloxane and octaphenylcyclotetrasiloxane.

Useful silanes, disilanes, or alkoxysilanes include organic substituted silanes having the general formula:

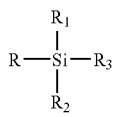

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenytrimethylsilane, triethylsilane and hexamethyldislane. Useful alkoxysilanes are those with at least one silicon-hydrogen bond.

Selectivation of the catalyst can also be accomplished using a combination of coke and silicon applied by the procedures described above.

Catalytic reforming involves the production of aromatics from a $C_{6+}$ paraffinic feed, e.g., naphtha, by contacting the feed with a reforming catalyst under reforming conditions to produce a reaction product comprising aromatics and paraffins. The reformate is formed under typical reforming conditions designed to promote dehydrogenation of naphthenes, isomerization of paraffinic hydrocarbons and dehydrocyclization of non-aromatic hydrocarbons.

Catalysts suitable for use in catalytic reforming include acidic reforming catalysts (bifunctional catalysts) and non-acidic reforming catalysts (monofunctional catalysts).

Acidic reforming catalysts usually comprise a metallic oxide support having disposed therein a Group VIII metal. Suitable metallic oxide supports include alumina and silica. Preferably, the acidic reforming catalyst comprises a metallic oxide support having disposed therein in intimate admixture a Group VIII metal (preferably platinum) and a metal promoter, such as rhenium, tin, germanium, cobalt, nickel, iridium, rhodium, ruthenium and combinations thereof. More preferably, the acidic reforming catalyst comprises an alumina support, platinum, and rhenium or platinum and tin on an alumina support.

Non-acidic or monofunctional reforming catalysts will comprise a non-acidic molecular sieve, e.g., zeolite, and one or more hydrogenation/dehydrogenation components. Examples of suitable molecular sieves include MFI structure type, e.g., silicalite, and molecular sieves having a large pore size, e.g., pore size from about 7 to 9 Angstroms. Examples of large pore molecular sieves include LTL, FAU, and *BEA structure types. Examples of specific molecular sieves include zeolite L, zeolite X, zeolite Beta, zeolite Y, and ETS-10.

The non-acidic catalysts will contain one or more hydrogenation/dehydrogenation metals, e.g., Group VII B metals, such as rhenium, and Group VIII metals, such as nickel, ruthenium, rhodium, palladium, iridium or platinum. The preferred Group VIII metal is platinum. Also, the non-acidic catalysts can contain a metal promoter such as tin.

The amount of hydrogenation/dehydrogenation metal present on the non-acidic catalyst will usually be from about 0.1% to about 5% of hydrogenation/dehydrogenation metal based on the weight of the catalyst. The metal can incorporated into the zeolite during synthesis of the zeolite, by impregnation, or by ion exchange of an aqueous solution containing the appropriate salt. By way of example, in an ion exchange process, platinum can be introduced by using cationic platinum complexes such as tetraammine-platinum (II) nitrate.

The non-acidic catalyst will usually include a binder. The binder can be a natural or a synthetically produced inorganic oxide or combination of inorganic oxides. Typical inorganic oxide supports which can be used include clays, alumina, and silica, in which acidic sites are preferably exchanged by cations that do not impart strong acidity.

The reforming process can be continuous, cyclic or semi-regenerative. The process can be in a fixed bed, moving bed, tubular, radial flow or fluid bed.

Conditions for reforming conditions include temperatures of at least about 400° C. to about 600° C. and pressures from about 50 psig (446 kPa) to about 500 psig (3,549 kPa), a mole ratio of hydrogen to hydrocarbons from 1:1 to 10:1 and a liquid hour space velocity of between 0.3 and 10.

Substantially any hydrocarbon feed containing $C_{6+}$ e.g., naphtha can be utilized. The naphtha will generally comprise $C_6$–$C_9$ aliphatic hydrocarbons. The aliphatic hydrocarbons may be straight or branched chain acyclic hydrocarbons, and particulary paraffins such as heptane.

Toluene/Benzene Methylation

The methylation reaction can be carried out in vapor phase or liquid phase. Also, the methylation reaction can be carried out in a fixed bed or fluidized bed.

Reaction conditions suitable for use in the present invention usually include temperatures from about 300° C. to about 700° C. and, preferably, from about 400° C. to about 700° C. Reaction pressures are usually between about 1 to about 1000 psig. The feed stream is passed over the catalyst at space velocities between about 0.1 and about 200 parts by weight of $C_6$–$C_7$ aromatic hydrocarbons, e.g., toluene, benzene, or mixtures thereof, per hour per part by weight of catalyst (W/hrW) and, preferably, between about 0.5 and about 100 parts by weight of $C_6$–$C_7$ aromatic hydrocarbons per hour per part by weight of catalyst. The molar ratio of toluene and benzene to methylating agent can vary and will usually be from about 0.1:1 to about 20:1. Preferred ratios for operation are in the range of 1:1 to about 4:1. The process is preferably conducted in the presence of hydrogen and/or added water such that the molar ratio of hydrogen and/or added water to $C_6$–$C_7$ aromatic hydrocarbons and methylating agent is between about 0.01 and about 100. Hydrogen gas can be supplied to the reaction as an anticoking agent and diluent. The methylating agent is usually supplied to the methylation reaction zone through multiple feed points, e.g., 3–6 feed points.

Typical methylating agents include methanol, dimethylether, methylchloride, methylbromide, methylcarbonate, acetaldehyde, dimethoxyethane, acetone, and dimethylsulfide. The methylating agent can also be formed from synthesis gas, e.g., the agent can be formed from the $H_2$, CO, and/or $CO_2$ of synthesis gas. The methylating agent can be formed from the synthesis gas within the methylation reaction zone. One skilled in the art will know that other methylating agents may be employed to methylate the benzene and/or toluene based on the description provided therein. Preferred methylating agents are methanol and dimethylether. Methanol is most preferred.

Catalysts suitable for use in the present invention include any catalyst that is effective for toluene or benzene methylation. The catalyst used in the process will usually comprise a crystalline molecular sieve.

The catalyst used in the methylation reaction will preferably comprise an intermediate pore size molecular sieve. Intermediate pore size molecular sieves have a pore size from about 5 to about 7 Å and include, for example, AEL, AFI, MWW, MFI, MEL, MFS, MEI, MTW, EUO, MTT, HEU, FER, and TON structure type zeolites. These materials are described in "Atlas of Zeolite Structure Types", eds. W. H. Meier, D. H. Olson, and Ch. Baerlocher, Elsevier, Fourth Edition, 1996, which is hereby incorporated by reference. Examples of suitable intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-5. Preferred molecular sieves are SAPO-11, as well as titanosilicate, gallosilicate, aluminosilicate, and gallium-containing aluminosilicate molecular sieves having a MFI structure.

The intermediate pore size molecular sieve will generally be a composition having the following molar relationship:

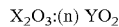

$$X_2O_3 : (n)\ YO_2$$

wherein X is a trivalent element such as titanium, aluminum, iron, boron, and/or gallium and Y is a tetravalent element such as silicon, tin, and/or germanium; and n has a value greater than 12, said value being dependent upon the particular type of molecular sieve. When the intermediate pore size molecular sieve is a MFI structure type molecular sieve, n is preferably greater than 10 and preferably, from 20:1 to 200:1.

When the molecular sieve has a gallium silicate composition, the molecular sieve usually will be a composition having the following molar relationship:

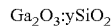

$$Ga_2O_3 : y SiO_2$$

wherein y is between about 20 and about 500. The molecular sieve framework may contain only gallium and silicon atoms or may also contain a combination of gallium, aluminum, and silicon.

Usually the molecular sieve will be incorporated with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 20 to about 50 percent.

The catalyst may also include at least one hydrogenation/dehydrogenation metal. Such metals can reduce the rate of deactivation of the catalyst. Reference to hydrogenation/dehydrogenation metal or metals is intended to encompass such metal or metals in the elemental state (i.e. zero valent) or in some other catalytically active form such as an oxide, sulfide, halide, carboxylate and the like. Such metals are known to persons skilled in the art and include, for example, one or more metals, and metals of Groups IIIA, IVA, VA, VIA, VIIA, VIII, IB, IIB, IIIB, IVB, VB, VIB, and VIIB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VA metals (i.e., Sb and Bi), and Group VIIB metals (i.e., Mn, Tc and Re). Noble metals (i.e., Pt, Pd, Ir, Rh, Os and Ru) are sometimes preferred.

When the catalyst used for the methylation reaction is a molecular sieve, the catalyst can be selectivated to enhance the amount of para-xylene produced by the methylation reaction by the use of a selectivating agent. Suitable selectivating agents include the selectivating agents disclosed earlier in this application for selectivating dehydrocyclooligomerization molecular sieve catalysts.

The catalyst can be subjected to steam treatment at a temperature of from about 800° C. to about 1200° C., preferably from about 950° C. to about 1050° C. with about 5% to about 100%, preferably from about 50% to about 100% steam, at a pressure of from about 0.1 to about 50 psia for about 0.1 to about 12 hours, preferably from about 3 to about 6 hours. A preferred catalyst for use in the present invention is disclosed in U.S. Pat. No. 6,423,879, which is hereby incorporated by reference.

Catalysts particularly suited for the methylation reaction are zeolite bound zeolite catalysts. These catalysts, as well as their method of preparation, are described in U.S. Pat. No. 5,994,603, which is hereby incorporated by reference. The zeolite bound zeolite catalysts will comprise first crystals of an acidic intermediate pore size first molecular sieve and a binder comprising second crystals of a second molecular sieve. Preferably, the zeolite bound zeolite catalyst contains less than 10 percent by weight based on the total weight of the first and second zeolite of non-zeolitic binder, e.g., amorphous binder. An example of such a catalyst comprises first crystals of a MFI or MEL structure type, e.g., ZSM-5 or ZSM-11, and a binder comprising second crystals of MFI or MEL structure type, e.g., Silicalite 1 or Silicalite 2.

The amount of benzene/toluene converted to xylenes will depend on a number of factors including the make up of the reformate to be methylated, the methylation conditions, and the catalyst used. Usually, at least 5 weight percent of the benzene/toluene will be converted to xylenes. Preferably, at least 7 weight percent of the benzene/toluene will be converted to xylenes, and, more preferably, at least 30 weight percent of the benzene/toluene will be converted to xylenes.

Also, the process of this invention may be used to produce greater than equilibrium amounts of para-xylene. Preferably, the process will produce a xylene product containing greater than 30 weight percent para-xylene based on the total weight of xylenes produced by the process. More preferably, the process produces a xylene product containing greater than 60 weight percent para-xylene based on the total weight of the xylenes produced by the process. Most preferably, the process produces a xylene product containing greater than 80 weight percent para-xylene based on the total weight of the xylenes produced by the process.

Even with the presence of up to 70 weight percent of $C_6$–$C_8$ non-aromatic hydrocarbons (based on the weight of the $C_6$–$C_7$ hydrocarbons present in the feed stream), the process of this invention can produce greater than equilibrium amounts of para-xylene from a feed stream containing the $C_6$–$C_7$ aromatic hydrocarbons (benzene, toluene or mixtures thereof). The feed stream will usually contain at least 0.2 weight percent of $C_6$–$C_8$ non-aromatic hydrocarbons (based on the weight of the $C_6$–$C_7$ aromatic hydrocarbons present in the feed stream). However, the amount of $C_6$–$C_8$ non-aromatic hydrocarbons will depend on a number of factors. For instance, the amount of $C_6$–$C_8$ non-aromatic hydrocarbons present in the feed stream will depend upon the type of catalytic reforming (continuous, cyclic or semi-regenerative) as well as the composition of the feed to the reformer. For example, reformate produced by CCR (continuous catalyst regeneration) will usually contain less $C_6$–$C_8$ non-aromatic hydrocarbons than reformate produced by other reforming technologies. Other reforming technologies usually have higher amounts of $C_6$–$C_8$ non-aromatic hydrocarbons, e.g., 10 to 20 weight percent of $C_6$–$C_8$ non-aromatic hydrocarbons and even as high as 70 weight percent.

The process is carried out by contacting the feed stream with a methylating agent under methylation conditions and in the presence of an acidic intermediate pore size molecular sieve, e.g., ZSM-5, catalyst. The $C_6$–$C_8$ non-aromatic hydrocarbons present in the feed stream are cracked to lower molecular weight products. Examples of these $C_6$–$C_8$ non-aromatic hydrocarbons include octane, 3-methylheptane, heptane, hexane, 2-methylpentane, 2,2-dimethylpentane, and 2-methylhexane.

For each pass of feed stream over the acidic intermediate pore size molecular sieve catalyst, usually at least 15 weight percent of the $C_6$–$C_8$ non-aromatic hydrocarbons present in the feed stream are cracked to lower molecular weight products. Preferably, at least 25 weight percent of the $C_6$–$C_8$ non-aromatic hydrocarbons are cracked to lower molecular weight products for each pass over the acidic intermediate pore size molecular sieve catalyst. More preferably, at least 30 weight percent of the $C_6$–$C_8$ non-aromatic hydrocarbons are cracked to lower molecular weight products for each pass over the acidic intermediate pore size molecular sieve catalyst.

The $C_6$–$C_8$ non-aromatic hydrocarbons not cracked when passed over the acidic intermediate pore size molecular sieve catalyst are usually collected and then recycled to the methylation zone and then passed over the the acidic para-selective intermediate pore size molecular sieve catalyst. Usually, the total amount of $C_6$–$C_8$ non-aromatic hydrocarbons are cracked to lower molecular weight products is at least 50 weight percent of the $C_6$–$C_8$ non-aromatic hydrocarbons. Preferably, at least 75 weight percent of the $C_6$–$C_8$ non-aromatic hydrocarbons are cracked to lower molecular weight products. More preferably, at least 90 weight percent of the $C_6$–$C_8$ non-aromatic hydrocarbons are cracked to lower molecular weight products and, most preferably, the resulting product is essentially free of $C_6$–$C_8$ non-aromatic hydrocarbons.

Also, in the practice of this embodiment, the methylating agent efficiency (the percent of methylating agent reacted to form xylenes is preferably at least 50 percent, more preferably at least 60 percent, and, most preferably, at least 75 percent. Preferably, this process produces a xylene product containing greater than 60 weight percent para-xylene based on the total weight of the xylenes produced by the process. More preferably, this process produces a xylene product containing greater than 80 weight percent para-xylene based on the total weight of the xylenes produced by the process.

EXAMPLE 1

A simulated naphtha reformate feed (naphtha reformate without hydrogen, $C_1$–$C_5$ hydrocarbons, and $C_{8+}$ hydrocarbons) was subjected to methylation using a zeolite bound zeolite catalyst. The simulated feed had the composition given below in Table 1:

TABLE 1

| Component | Wt. % |
| --- | --- |
| $C_{5-}$ | 0.00 |
| n-$C_6$ | 33.12 |
| i-$C_6$ | 3.69 |
| n-$C_7$ | 0.00 |
| i-$C_7$ | 0.00 |
| Benzene | 15.85 |
| Toluene | 47.35 |
| PX | 0.00 |
| MX | 0.00 |
| OX | 0.00 |
| EB | 0.00 |
| $C_{9+}$ | 0.00 |
| Total | 100 |

The catalyst used for the test comprised 70 wt. % H-ZSM-5 core crystals (average particle size of 3.5 microns) having a silica to alumina mole ratio of 75:1 and 30 wt. % ZSM-5 binder crystals having a silica to mole ratio of approximately 900:1. The catalyst was prepared by first mixing the ZSM-5 core crystals with amorphous silica containing a trace amount of alumina and then extruding the mixture into a silica bound extrudate. Next, the silica binder of the extrudate was converted to the second zeolite by aging the aggregate at elevated temperatures in an aqueous solution containing a template and hydroxy ions sufficient to covert the silica to the binder crystals. The resulting zeolite bound zeolite was then washed, dried, calcined, and ion exchanged into the hydrogen form.

The methylation was carried out under the conditions shown below in Table 2:

TABLE 8

| Component | |
| --- | --- |
| WHSV ($h^{-1}$) | 9.2 |
| MeOH/:Toluene [molar] | 0.37 |
| H2:(MeOH + HCs) [molar] | 2 |
| Pressure (psig) | 200 |
| Temperature (° F.) | 900 |

The test was carried out by loading the catalyst into a fixed bed reactor and heating the catalyst in flowing hydrogen at reactor temperature range from room temperature to 950° F. for two hours. Next, the feed was introduced into the reactor and the test was carried out at the conditions shown in Table 2. The results of the test are set forth below in Table 3.

TABLE 3

| Component | Wt. % |
| --- | --- |
| $C_{5-}$ | 1.94 |
| $n\text{-}C_6$ | 31.88 |
| $i\text{-}C_6$ | 3.48 |
| $n\text{-}C_7$ | 0.00 |
| $i\text{-}C_7$ | 0.00 |
| Benzene | 14.38 |
| Toluene | 43.11 |
| PX | 4.12 |
| MX | 0.29 |
| OX | 0.10 |
| EB | 0.23 |
| $C_{9+}$ | 0.46 |
| Total | 100 |

The results in Table 3 shows that after methylation, the content of the reformate increased from no xylenes being present to 4.51% xylenes. Also, the amount of para-xylene produced (91% para-xylene) was greater than equilibrium amounts (24% para-xylene).

EXAMPLE 2

A simulated light naphtha reformate feed was subjected to toluene methylation. The catalyst used in the test comprised ¹⁄₁₆ inch extrudates which contained 65 weight percent H-ZSM-5 and 35 weight percent silica binder. The catalyst had an alpha value of 330. The "alpha value" of a catalyst is an approximate indication of its catalytic cracking activity. The alpha test is described in U.S. Pat. No. 3,354,078 and in the *Journal of Catalysis,* Vol. 4, 522–529 (1965); Vol. 6, 278 (1966); and Vol. 61, 395 (1980), each incorporated herein by reference to that description.

The reformate feed used in the test had the composition given below:

TABLE 4

| Component | Wt. % |
| --- | --- |
| $C_{5-}$ | 0.00 |
| $n\text{-}C_6$ | 18.58 |
| $i\text{-}C_6$ | 15.04 |
| $n\text{-}C_7$ | 4.30 |
| $i\text{-}C_7$ | 5.37 |
| Benzene | 15.32 |
| Toluene | 41.38 |
| PX | 0.00 |
| MX | 0.00 |
| OX | 0.00 |
| EB | 0.00 |
| $C_{9+}$ | 0.00 |
| Total | 100 |

The test was carried out under the following conditions:

TABLE 5

| Component | |
| --- | --- |
| WHSV ($h^{-1}$) | 1 |
| MeOH/:Toluene [molar] | 1 |
| H2:(MeOH + HCs) [molar] | 1 |
| Pressure (psig) | 64 |
| Temperature (° F.) | 700 |

The test was carried out by loading the catalyst into a fixed bed reactor and heating the catalyst in flowing hydrogen at reactor temperature range from room temperature to 950° F. for two hours. Next, the reformate was introduced into the reactor and the test was carried out under the conditions shown in Table 5. The results of the test are set forth below in Table 6.

TABLE 6

| Component | Wt. % |
| --- | --- |
| $C_{5-}$ | 1.13 |
| $n\text{-}C_6$ | 16.58 |
| $i\text{-}C_6$ | 13.43 |
| $n\text{-}C_7$ | 3.87 |
| $i\text{-}C_7$ | 4.33 |
| Benzene | 11.06 |
| Toluene | 35.82 |
| PX | 2.59 |
| MX | 3.20 |
| OX | 3.76 |
| EB | 0.00 |
| $C_{9+}$ | 4.23 |
| Total | 100 |

The results report in Table 6 shows that after toluene methylation, the content of the reformate increased from no xylenes being present to 9.49% xylenes. Also, the amount of para-xylene produced (27% para-xylene) was greater than an equilibrium amount (24% para-xylene).

EXAMPLE 3

A simulated light reformate, which would be formed by the dehydrocyclo-oligomerization of $C_2$–$C_5$ aliphatic hydrocarbons, was subjected to toluene methylation. The catalyst used in the test had an alpha value of approximately 22 and comprised ¹⁄₁₆ inch extrudates which contained 65 wt. % H-ZSM-23 having a silica to alumina mole ratio of 110:1 and 35 wt. % of alumina binder. The ZSM-23 was prepared according to U.S. Pat. No. 4,076,842.

The reformate feed used in the test had the composition given below:

TABLE 7

| Component | Wt. % |
| --- | --- |
| $C_{5-}$ | 0.00 |
| $n\text{-}C_6$ | 0.00 |
| $i\text{-}C_6$ | 0.00 |
| $n\text{-}C_7$ | 35.00 |
| $i\text{-}C_7$ | 5.00 |
| Benzene | 15.00 |
| Toluene | 45.00 |
| PX | 0.00 |
| MX | 0.00 |
| OX | 0.00 |
| EB | 0.00 |
| $C_{9+}$ | 0.00 |
| Total | 100 |

The test was carried out under the following conditions:

TABLE 8

| Component | |
| --- | --- |
| WHSV ($h^{-1}$) | 8 |
| MeOH/:Toluene [molar] | 1/3 |
| H2:(MeOH + HCs) [molar] | 2 |
| Pressure (psig) | 150 |
| Temperature (° F.) | 932 |

The test was carried out by loading the catalyst into a fixed bed reactor and heating the catalyst in flowing hydrogen to the reaction temperature. Next, the reformate was introduced into the reactor and the test was run at the conditions shown in Table 8. The results of the test are set forth below in Table 9.

TABLE 9

| Component | Wt. % |
|---|---|
| $C_{5-}$ | 19.25 |
| n-$C_6$ | 0.00 |
| i-$C_6$ | 0.00 |
| n-$C_7$ | 16.10 |
| i-$C_7$ | 4.65 |
| Benzene | 13.07 |
| Toluene | 41.45 |
| PX | 2.74 |
| MX | 1.83 |
| OX | 0.91 |
| EB | 0.00 |
| $C_{9+}$ | 0.00 |
| Total | 100 |

The results in Table 9 shows that after toluene methylation, the content of the reformate increased from no xylenes being present to 5.48% xylenes. Also, the amount of para-xylene produced (50% para-xylene) was greater than an equilibrium amount (24% para-xylene).

EXAMPLE 4

A simulated light reformate, which would be formed by the dehydrocyclo-oligomerization of $C_2$–$C_5$ aliphatic hydrocarbons, was subjected to toluene methylation using a SAPO-11 catalyst. The catalyst had an alpha value of approximately 52 and its chemical analysis was $Si_{.1}Al_{.46}P_{.44}$. The SAPO-11 was prepared according to U.S. Pat. No. 6,294,493

The reformate feed used in the test had the composition given below:

TABLE 10

| Component | Wt. % |
|---|---|
| $C_{5-}$ | 0.00 |
| n-$C_6$ | 0.00 |
| i-$C_6$ | 0.00 |
| n-$C_7$ | 35.00 |
| i-$C_7$ | 5.00 |
| Benzene | 15.00 |
| Toluene | 45.00 |
| PX | 0.00 |
| MX | 0.00 |
| OX | 0.00 |
| EB | 0.00 |
| $C_{9+}$ | 0.00 |
| Total | 100 |

The test was carried out under the following conditions:

TABLE 11

| Component | |
|---|---|
| WHSV ($h^{-1}$) | 8 |
| MeOH/:Toluene [molar] | 1/3 |
| H2:(MeOH + HCs) [molar] | 2 |
| Pressure (psig) | 150 |
| Temperature (° F.) | 932 |

The test was carried out by loading the catalyst into a fixed bed reactor and heating the catalyst in flowing hydrogen to the reaction temperature. Next, the reformate was introduced into the reactor and the test was run at the conditions shown in Table 11. The results of the test are set forth below in Table 12.

TABLE 12

| Component | Wt. % |
|---|---|
| $C_{5-}$ | 19.25 |
| n-$C_6$ | 0.00 |
| i-$C_6$ | 0.00 |
| n-$C_7$ | 16.10 |
| i-$C_7$ | 4.65 |
| Benzene | 13.07 |
| Toluene | 41.45 |
| PX | 2.74 |
| MX | 1.83 |
| OX | 0.91 |
| EB | 0.00 |
| $C_{9+}$ | 0.00 |
| Total | 100 |

The results in Table 12 shows that after toluene methylation, the content of the reformate increased from no xylenes being present to 5.8% xylenes. Also, the amount of para-xylene produced >40% para-xylene, was greater than an equilibrium amount (24% para-xylene).

EXAMPLE 5

A simulated full range naphtha reformate (without $C_1$–$C_5$ hydrocarbons) was subjected to toluene methylation using a silica selectivated H-ZSM-5/silica bound catalyst.

The catalyst was selectivated by contacting H-ZSM-5/silica bound (65 weight % H-ZSM-5 35 weight % silica) with dimethylphenylmethyl polysiloxane dissolved in decane and subsequently calcining the selectivated catalyst. The catalyst was treated with 3 additional silicon selectivation treatments using substantially the same procedure. The catalyst had an alpha value of approximately 300.

The reformate feed used in the test had the composition given below:

TABLE 13

| Component | Wt. % |
|---|---|
| $C_{5-}$ | 0.00 |
| n-$C_6$ | 33.12 |
| i-$C_6$ | 3.69 |
| n-$C_7$ | 0.00 |
| i-$C_7$ | 0.00 |
| Benzene | 15.85 |
| Toluene | 47.35 |
| PX | 0.00 |
| MX | 0.00 |
| OX | 0.00 |
| EB | 0.00 |
| $C_{9+}$ | 0.00 |
| Total | 100 |

The test was carried out under the following conditions:

TABLE 14

| Component | |
|---|---|
| WHSV (h$^{-1}$) | 9.2 |
| MeOH/:Toluene [molar] | 0.37 |
| H2:(MeOH + HCs) [molar] | 2 |
| Pressure (psig) | 200 |
| Temperature (° F.) | 900 |

The test was carried out by loading the catalyst into a fixed bed reactor and heating the catalyst in flowing hydrogen at a reactor temperature range from room temperature to 950° F. for two hours. Next, the reformate was introduced into the reactor and the test was run at the conditions shown in Table 14. The product contained more than 90% para-xylene based on the total amount of xylenes present in the product.

EXAMPLE 6

A fluid bed catalyst was produced that comprised about 4 wt % phosphorous and 10 wt % of ZSM-5 having a silica to alumina mole ratio of 450 to 1. The remainder of the catalyst comprised a binder comprised of silica-alumina, and clay. The catalyst was steamed at 1000° C. for 45 minutes prior to use. The catalyst had a particle density of 1.4 g/cc and a median particle size between 70–80 microns. The catalyst was loaded into a 4" diameter by 27' high fluid bed pilot plant which operated with continuous catalyst circulation between a reaction zone and a regeneration zone. The regeneration zone removed coke by combustion with air and enabled constant catalyst activity to be maintained in the reaction zone. The feed to the reactor comprised a $C_7$ heart-cut fraction isolated from reformate via distillation. The $C_7$ reformate contained 91.8 wt % toluene and 6.2 wt % $C_7$–$C_8$ non-aromatics. The methylation was carried out under conversion conditions. The para-xylene selectivity was greater than 85% and the yield on toluene was 27 wt %. at high toluene conversion. The efficiency of converting methanol to xylenes remained in excess of 60 mol % even with over 5 wt % non-aromatics in the feed. Surprisingly, the high conversion of non-aromatic co-boilers did not produce $C_8$ and $C_9$ paraffins, olefins, or naphthenes and degrade of the para-xylene product quality.

What is claimed is:

1. A process for the production of para-xylene, which process comprises:
   (a) providing a reformate comprising: (i) hydrogen; (ii) $C_1$–$C_5$ hydrocarbons, (iii) $C_6$–$C_7$ aromatic hydrocarbons comprising benzene, toluene or mixtures thereof (iv) $C_{8+}$ aromatic hydrocarbons; and, (v) and from 0.2 to about 20 weight percent of non-aromatic $C_6$–$C_8$ hydrocarbons based on the weight of the $C_6$–$C_7$ aromatic hydrocarbons present in the reformate; and
   (b) methylating at least a portion of said benzene, toluene, or mixtures thereof present in said reformate in a methylation reaction zone with a methylating agent under vapor phase conditions effective for the methylation and in the presence of an acidic molecular sieve catalyst comprising an intermediate pore size molecular sieve to produce a resulting product having a higher xylenes content than said reformate;
   wherein: (I) at least 7 weight percent of the benzene and/or toluene present in said reformate is converted to xylenes; and, (II) at least 50 weight percent of said $C_6$–$C_8$ non-aromatic hydrocarbons present in said reformate are cracked to lower molecular weight products.

2. The process recited in claim 1, wherein said acidic molecular sieve catalyst is para-selective.

3. The process recited in claim 2, wherein at least 60 percent of the xylenes produced in the methylation are para-xylene.

4. The process recited in claim 3, wherein said reformate is formed by the catalytic reforming.

5. The process of claim 4, further comprising removing from said reformate at least a portion of said hydrogen, said $C_1$–$C_5$ hydrocarbons, and said $C_{8+}$ aromatic hydrocarbons.

6. The process of claim 4, wherein substantially all of the $C_1$–$C_5$ hydrocarbons and the $C_{8+}$ aromatic hydrocarbons are removed from said reformate before methylation.

7. The process recited in claim 4, wherein said intermediate pore size molecular sieve is selected from the group consisting of ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-11.

8. The process recited in claim 7, wherein said molecular sieve is ZSM-5.

9. The process recited in claim 4, wherein hydrogen is supplied to said methylation reaction zone.

10. The process recited in claim 4, said methylation is conducted in the presence of hydrogen and/or added water such that the molar ratio of hydrogen and/or added water to $C_6$–$C_7$ aromatic hydrocarbons and methylating agent is between about 0.01 and about 100.

11. The process recited in claim 6, wherein step (b) is carried out in a fluidized bed.

12. The process recited in claim 6, wherein step (b) is carried out in a fixed bed.

13. The process recited in claim 4, wherein said methylation conditions include a temperature from about 400° C. to about 700° C., a pressure from about 1 to 1000 psig, and a molar ratio of methylating agent to toluene and benzene between about 0.1:1 to about 20:1.

14. The process recited in claim 13, wherein said feed stream is passed over said para-selective molecular sieve catalyst at a space velocity between about 0.1 and about 100 parts by weight of $C_6$–$C_7$ aromatic hydrocarbons.

15. The process recited in claim 7, wherein said para-selective molecular sieve catalyst is treated with 50% to about 100% steam at a temperature of from about 800° C. to about 1200° C., at a pressure of from about 0.1 to about 50 psia for a period of about 0.1 to about twelve hours.

16. The process recited in claim 7, wherein said reformate is produced by continuous catalyst regeneration.

17. The process recited in claim 7, wherein said para-selective molecular sieve catalyst comprises a selectivating agent.

18. The process recited in claim 17, wherein said a selectivating agent is selected from the group consisting of silica, coke, phosphorus, alkaline earth metal oxides, rare earth metal oxides, lanthanum oxide, boron oxide, titania, antimony oxide, manganese oxide, and mixtures thereof.

19. The process recited in claim 18, wherein said molecular sieve is ZSM-5.

20. The process recited in claim 4, further comprising the step of recovering the para-xylene from said resulting product.

21. The process recited in claim 4, wherein said methylating agent is selected from the group consisting of methanol, dimethylether, methylchloride, methylbromide, methylcarbonate, acetaldehyde, dimethoxyethane, acetone, and dimethylsulfide.

22. The process recited in claim 21, wherein said methylating agent is injected into said methylation reaction zone through more than one feed point.

23. The process recited in claim 4, wherein at least 7 weight percent of the benzene and/or toluene present in said reformate is converted to xylenes.

24. The process recited in claim 4, wherein the resulting product contains contains more than 75 weight percent of para-xylene based on the total weight of the xylenes produced by said process.

25. The process recited in claim 4, wherein the amount of methylating agent reacted to form xylenes is at least 50 percent.

26. The process recited in claim 4, wherein the resulting product contains more than 80 weight percent of para-xylene based on the total weight of the xylenes produced by said process.

27. The process recited in claim 3, wherein said reformate is formed by the dehydrocyclo-oligomerization of $C_2$–$C_5$ aliphatics.

28. The process recited in claim 3, wherein said reformate is formed by the cracking of hydrocarbons.

29. The process recited in claim 27, wherein said cracking of hydrocarbons is accomplished in a catalytic cracking process.

30. The process recited in claim 3, wherein said cracking of hydrocarbons is accomplished in a steam cracking process.

31. The process recited in claim 8, wherein at least 90 weight percent of said $C_6$–$C_8$ non-aromatic hydrocarbons present in said reformate are cracked to lower molecular weight products.

32. The process recited in claim 8, wherein said resulting product is essentially free of said $C_6$–$C_8$ non-aromatic hydrocarbons.

33. The process recited in claim 31, wherein the resulting product contains greater than 80 weight percent of para-zylene based on the total weight of the xylenes produced by said process.

34. The process recited in claim 33, wherein at least 30 weight percent of the benzene and/or toluene present in said reformate is converted to xylenes.

* * * * *